(12) United States Patent
Py

(10) Patent No.: US 7,092,175 B2
(45) Date of Patent: Aug. 15, 2006

(54) CONTACT LENS TRANSFER DEVICE AND ASSOCIATED METHOD

(75) Inventor: Daniel Py, Stamford, CT (US)

(73) Assignee: Medical Instill Technologies, Inc., New Milford, CT (US)

( * ) Notice: Subject to any disclaimer, the term of this patent is extended or adjusted under 35 U.S.C. 154(b) by 0 days.

(21) Appl. No.: 10/990,660

(22) Filed: Nov. 16, 2004

(65) Prior Publication Data

US 2005/0127693 A1    Jun. 16, 2005

Related U.S. Application Data

(60) Provisional application No. 60/520,609, filed on Nov. 17, 2003.

(51) Int. Cl.
*G02B 7/02* (2006.01)

(52) U.S. Cl. .......................... 359/819; 134/21; 134/34

(58) Field of Classification Search .................. 359/819, 359/821, 822, 793, 811, 813, 818; 134/34, 134/21, 32, 104.1
See application file for complete search history.

(56) References Cited

U.S. PATENT DOCUMENTS

| | | | |
|---|---|---|---|
| 2,919,696 A | 1/1960 | Rinaldy | |
| 3,091,328 A | 5/1963 | Leonardos | 206/5.1 |
| 3,139,298 A | 6/1964 | Grabiel | 294/1.2 |
| 3,304,113 A | 2/1967 | Hutchison | 294/1.2 |
| 3,879,076 A | 4/1975 | Barnett | 294/1.2 |
| 3,910,618 A | 10/1975 | Massenz | 294/1.2 |
| 4,037,866 A | 7/1977 | Price | 294/1.2 |
| 4,071,272 A | 1/1978 | Drdlik | |
| 4,093,291 A | 6/1978 | Schurgin | |
| 4,113,297 A | 9/1978 | Quinn | |
| 4,200,320 A | 4/1980 | Durham | |
| 4,201,408 A | 5/1980 | Tressel | |
| 4,244,466 A | 1/1981 | Arnhem | |
| 4,308,947 A | 1/1982 | Arnhem | |
| 4,378,126 A | 3/1983 | Procenko | |
| 4,387,921 A | 6/1983 | Licata | |
| 4,565,396 A | 1/1986 | Larimer | |
| 4,792,334 A | 12/1988 | Py | 604/295 X |
| 4,908,024 A | 3/1990 | Py | |
| 4,946,452 A | 8/1990 | Py | 604/301 |
| 4,981,479 A | 1/1991 | Py | 604/300 X |
| 5,069,494 A | 12/1991 | Reinson et al. | 294/1.2 |
| 5,085,651 A | 2/1992 | Py | 604/298 |
| 5,133,702 A | 7/1992 | Py | 604/300 X |
| 5,163,929 A | 11/1992 | Py | 604/298 |
| 5,246,259 A | 9/1993 | Hellenkamp et al. | 294/1.2 |

(Continued)

FOREIGN PATENT DOCUMENTS

DE    2434319 B1    1/1976

(Continued)

*Primary Examiner*—Timothy Thompson
(74) *Attorney, Agent, or Firm*—McCarter & English, LLP

(57) ABSTRACT

A contact lens transfer device for transferring a contact lens from a storage container to a contact lens applicator has a body and a contact lens holder movably mounted on the body. The contact lens holder defines a contact lens support surface, a fluid-flow aperture extending through the contact lens support surface, and a chamber coupled in fluid communication with the fluid-flow aperture. A contact lens is removably receivable on the lens support surface, and the fluid-flow aperture is coupled in fluid communication with an interface between the contact lens and lens support surface for introducing fluid from the chamber, through the fluid-flow aperture and into the interface to release the lens from the lens support surface.

17 Claims, 3 Drawing Sheets

U.S. PATENT DOCUMENTS

| | | | | |
|---|---|---|---|---|
| 5,267,986 | A | 12/1993 | Py | 604/294 |
| 5,300,115 | A | 4/1994 | Py | 623/5.15 |
| 5,320,845 | A | 6/1994 | Py | 424/427 |
| 5,366,499 | A | 11/1994 | Py | 424/405 |
| 5,401,259 | A | 3/1995 | Py | 604/294 |
| 5,407,241 | A | 4/1995 | Harrison | 294/1.2 |
| 5,538,301 | A | 7/1996 | Yavitz et al. | 294/1.2 |
| 5,558,374 | A | 9/1996 | Harrison | 294/1.2 |
| 5,613,957 | A | 3/1997 | Py | 604/294 |
| 5,649,727 | A | 7/1997 | St. Louis | 294/1.2 |
| 5,685,869 | A | 11/1997 | Py | 604/294 |
| 5,688,007 | A | 11/1997 | Jefferson | 294/1.2 |
| 5,695,049 | A | 12/1997 | Bauman | 206/5.1 |
| 5,732,990 | A | 3/1998 | Yavitz et al. | 294/1.2 |
| 5,875,931 | A | 3/1999 | Py | 222/137 |
| 5,913,556 | A | 6/1999 | Perusse | 294/1.2 |
| 5,944,702 | A | 8/1999 | Py | 250/352 |
| 6,033,384 | A | 3/2000 | Py | |
| RE37,047 | E | 2/2001 | Py | |
| 6,213,982 | B1 | 4/2001 | Py | |
| 6,401,915 | B1 | 6/2002 | Faxe | |
| 6,739,636 | B1 | 5/2004 | Py | |
| 2004/0074525 | A1* | 4/2004 | Widman et al. | 134/34 |

FOREIGN PATENT DOCUMENTS

| | | |
|---|---|---|
| DE | 3822654 A1 | 1/1990 |
| DE | 3920919 A1 | 1/1990 |
| FR | 1401116 | 4/1965 |
| FR | 2481472 | 10/1981 |
| FR | 2496906 | 6/1982 |
| FR | 2525472 | 10/1983 |
| GB | 2001778 A | 2/1979 |
| JP | 61018920 | 1/1986 |
| JP | 02023960 | 1/1990 |
| WO | WO 81/02287 | 8/1981 |
| WO | WO 93/04648 | 3/1993 |
| WO | WO 01/10367 | 8/2000 |

* cited by examiner

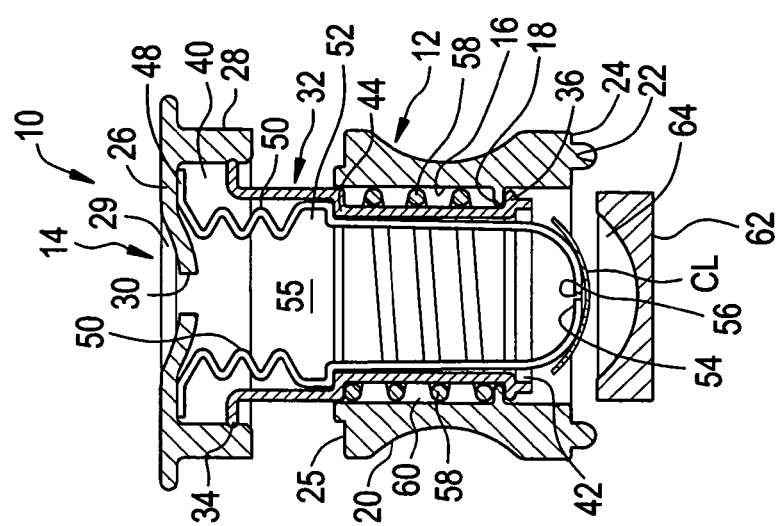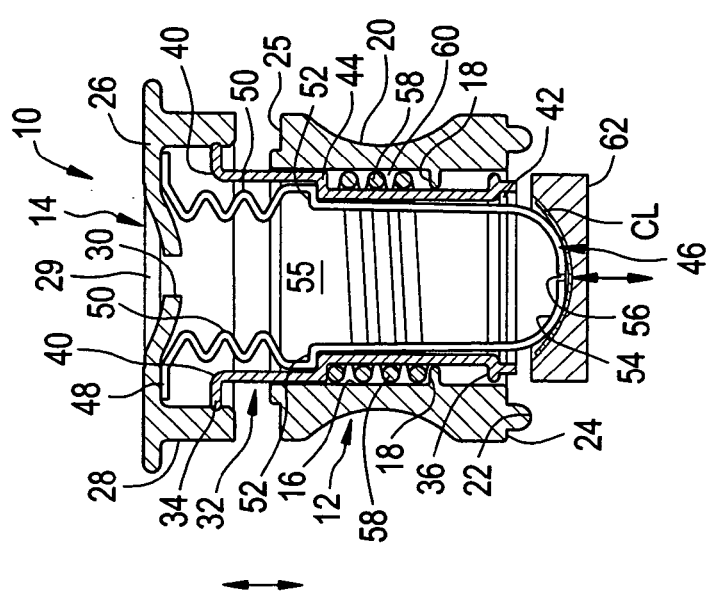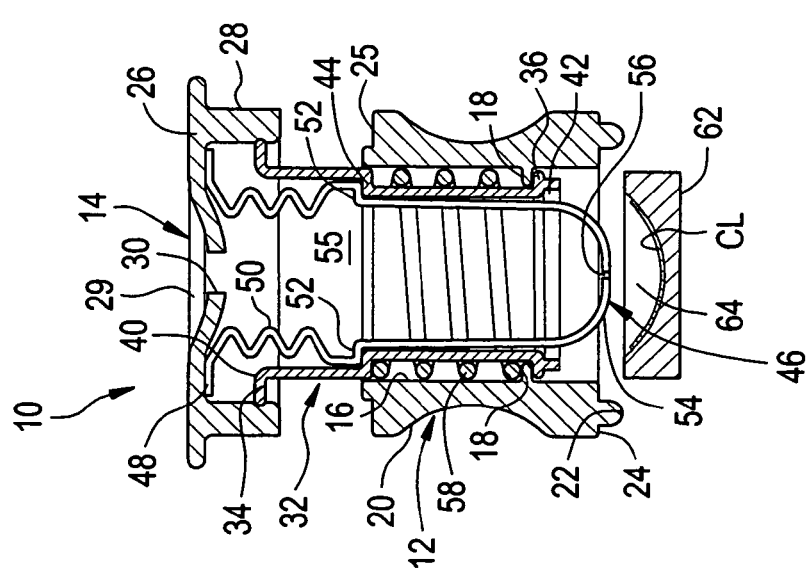

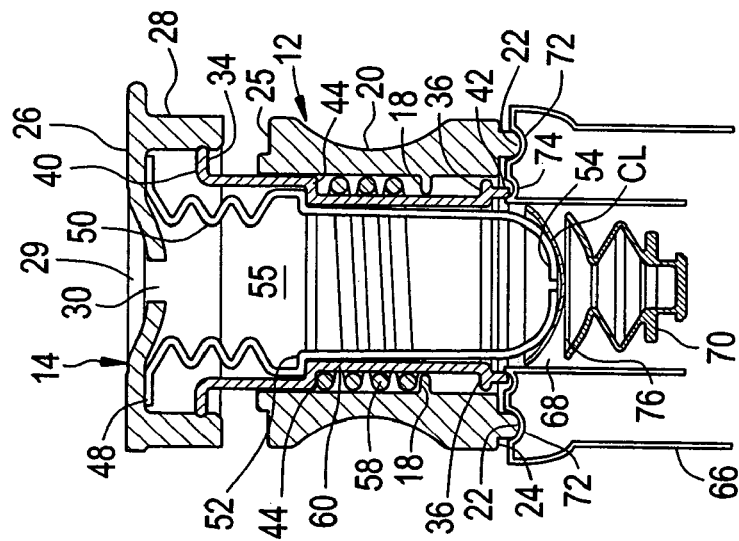
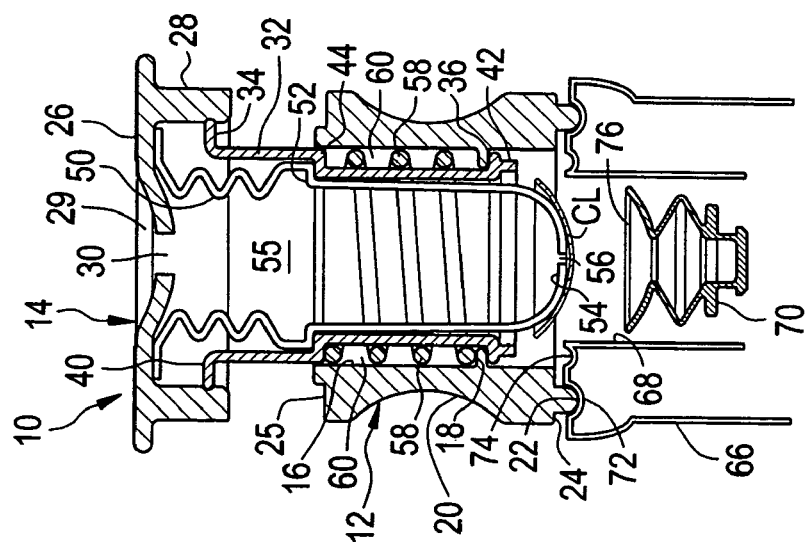
FIG. 2A  FIG. 2B  FIG. 2C

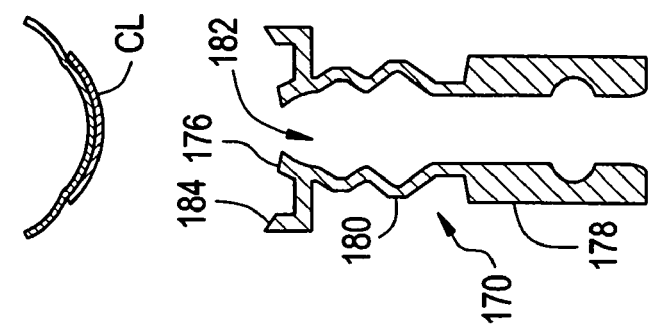
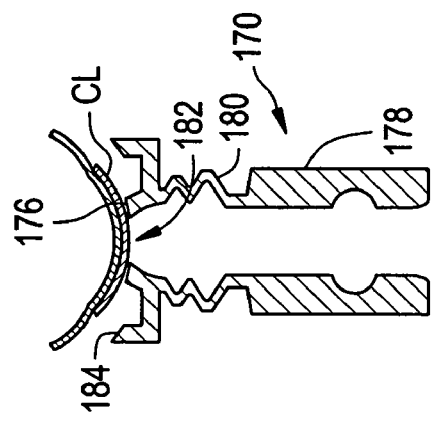
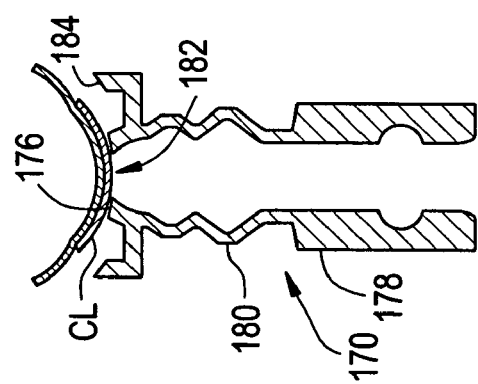
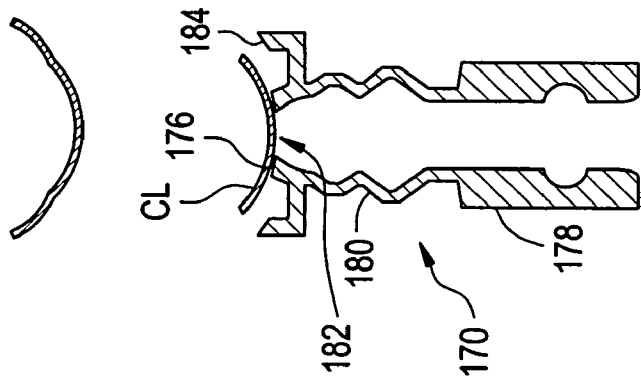

CONTACT LENS TRANSFER DEVICE AND ASSOCIATED METHOD

CROSS REFERENCE TO RELATED APPLICATION

This patent application claims the benefit of U.S. Provisional Patent Application Ser. No. 60/520,609, filed Nov. 17, 2003, which is hereby expressly incorporated by reference as part of the present disclosure.

FIELD OF THE INVENTION

The present invention relates to devices for manipulating contact lenses, and more particularly, to devices for transferring contact lenses from a storage container, such as a blister pack or lens holder, onto a contact lens applicator.

BACKGROUND OF THE INVENTION

Many patients who require optical correction for visual acuity wear eye-glasses because they either cannot, or do not desire to apply contact lenses to their eyes. Among those who are able to apply contact lenses to their eyes without assistance, it is believed that approximately 25% of these patients have terminated use of contact lenses because of complications arising from a lack of aseptic conditions and/or because of frustrations or difficulties arising from the need to clean and store the contact lenses, and transport with themselves the necessary containers and cleaning solutions to maintain the contact lenses. For example, the containers for holding contact lenses need to be carefully cleaned and are difficult, and in many cases, impossible to adequately clean. In addition, these persons typically require a mirror to apply the contact lenses, and because they have difficulty viewing themselves within the mirror without eyeglasses, they have further difficulty applying the contact lenses to their eyes without assistance.

Many ocular complications relating to contact lenses are due to infections and/or toxic reactions arising from incomplete rinsing of the contact lenses with cleaning solutions or otherwise inadequate cleaning or not maintaining the sterile conditions of the lenses prior to application to the eyes. A certain number of such complications are due to the preservatives contained within the cleaning solutions. For example, it has been widely demonstrated that certain preservatives are aggressive, irritating and/or damaging to the superficial layers of the cornea of the eye.

There are numerous events that must be carried out to properly apply contact lenses to a person's eyes, including: forcing the upper and lower eyelids in a wide-open position so that the contact lens (typically about 14.5 mm in outer diameter) can fit through the opening between the eyelids; adequately cleaning the finger(s) used to handle and apply the contact lens; making sure the contact lens is properly oriented with the correct side (or concave side) facing the eye; making sure the contact lens is in a state of equilibrium on the finger at the time of application; and applying the contact lens onto the cornea of the eye without irritating the cornea or otherwise causing the eye to blink during application. The sensitivity of the cornea is among the highest of the human tissues, and therefore if the eyelids are not maintained in the proper position during application of the contact lens, the maneuver fails.

In view of the above, several attempts have been made to aid a person when applying a contact lens. For example, U.S. Pat. No. 2,919,696 to Rinaldy shows an instrument for applying a contact lens. The instrument has a cup member 11 with a rim 13. A bracket 14 supports a lens supporting element 20 which is slidably mounted within the cup member 11. In use, the lens supporting element 20 is retracted and retains the lens by surface tension. The rim 13 is manually deformed and placed against the eyelids so that upon relaxing the rim 13, the eyelids are retained open. Subsequently, the lens supporting element 20 is depressed to place the contact lens on the eye and the instrument is removed.

U.S. Pat. No. 3,910,618 to Massenz provides a contact lens applicator having a cup 11 connected to an irrigation bottle 23 by a tube 14. The tube 14 slides within the cup 11 and communicates fluid into the cup 11 from the irrigation bottle 23. The end of the tube within the cup 11 has a lens seat 19 for receiving a contact lens. The distal end of the cup 11 is a rim 12. Both the rim 12 and the cup are made of rubber. In operation, the rim 12 is squeezed to bring the outer edges together. The rim 12 is applied to the eyelid. Upon relief of the compression, the cup 11, being resilient, resumes shape keeping the eye widely exposed. Then, the tube 14 is moved toward the eye to place a contact lens thereon and the irrigation bottle 23 provides fluid as desired.

U.S. Pat. No. 4,113,297 to Quinn illustrates a device for inserting and removing a contact lens 32. A stand 11 supports the device upright on a flat surface. A storage chamber 15 is in fluid communication with a float chamber 14. An applicator eyepiece 16 mounts on top of the float chamber 14 and defines an aperture. A rod member 20 extends through the aperture and receives a contact lens on its top. The height of the rod member 20 is determined by the fluid level within the float chamber 14. Actuation of a flexible portion of the storage chamber 15 varies the fluid level within the float chamber 14 and, thus, the height of the rod member 20. To apply a contact lens, the fingers of one hand are used to hold the eye open over the eyepiece 16. The free hand actuates the storage chamber 15 to raise the rod member 20 to place the contact lens on the eye.

U.S. Pat. No. 5,069,494 to Reinson et al. shows a contact lens applicator 25 which also stores a plurality of contact lens. The container portion 10 includes multiple portions 10 which are identical and interlocking. Each portion 10 contains a single contact lens disposed in a liquid. The lens is supported on a deformable projection made of five legs 20. The portions 10 have a cover surface 16 and sidewalls with inner threads 13 and outer threads 14. The inner threads 13 and outer threads 14 of adjacent portions 10 threadably engage such that the adjacent portion 10 defines the cover for the next adjacent portion 10. A base 12 upon which the contact lens rests completes the portions 10.

One of the drawbacks associated with such prior art devices and methods is contamination of the contact lens by, for example, a user's fingers. Another drawback associated with such prior art devices and methods is the significant level of skill and/or dexterity that may be required to properly manipulate the lens.

Accordingly, it is an object of the present invention to overcome one or more of the above-described drawbacks and/or disadvantages of such prior art devices and methods.

SUMMARY OF THE INVENTION

Exemplary embodiments of the invention include a contact lens transfer device for transferring a contact lens from a storage container to a contact lens applicator and related method for transferring contact lenses. The contact lens transfer device comprises a body, and a contact lens holder movably mounted on the body. The contact lens holder includes a contact lens support surface, at least one fluid-flow aperture extending through the contact lens support surface, and a chamber coupled in fluid communication with the at least one fluid-flow aperture. A contact lens is removably receivable on the lens support surface, and the at least one fluid-flow aperture is coupled in fluid communication with an interface between the contact lens and lens support surface for introducing fluid from the chamber, through the fluid-flow aperture, and into the interface to release the lens from the lens support surface.

In one embodiment of the present invention, the lens support surface is substantially convex, and defines a fluid-flow aperture extending through an approximately central portion thereof. In this embodiment, the lens holder includes at least one movable portion coupled in fluid communication with the chamber and movable to, in turn, move fluid from the chamber, through the fluid-flow aperture, and into the interface between the contact lens support surface and a contact lens received thereon. In one embodiment of the present invention, the movable portion is defined by a bellows.

In one embodiment of the present invention, the contact lens transfer device further comprises an approximately tubular support mounted between the lens holder and body for supporting the lens holder within the body. Also in this embodiment, a spring is coupled between the tubular support and body for biasing the tubular support in a direction outwardly of the body. An actuator is coupled to the lens holder for moving the lens holder between (i) a retracted position, and (ii) an extended position for at least one of removing a contact lens from a storage container onto the lens support surface of the lens holder, and releasing the lens from the lens support surface onto a surface of a contact lens applicator. Also in this embodiment of the present invention, the actuator is a button defining a peripheral flange that slidably receives therein at least a portion of each of the tubular support and lens holder.

The present invention also is directed to a method for transferring a contact lens from a storage container to a contact lens applicator, comprising:

(i) manually engaging a contact lens transfer device;

(ii) placing a lens support surface of the contact lens transfer device into contact with a contact lens received within a storage container;

(iii) removing the lens support surface with the contact lens seated thereon from the storage container;

(iv) positioning the lens support surface with the contact lens seated thereon adjacent to a lens holder of a contact lens applicator; and (v) introducing a fluid into an interface between the lens support surface and contact lens seated thereon and, in turn, releasing the contact lens from the lens support surface and transferring the contact lens from the lens support surface onto the lens holder of the contact lens applicator.

One advantage of the contact lens transfer device and method of the present invention is that a user can transfer contact lenses from a lens storage container to a contact lens applicator without the user's fingers or hands touching the lens. As a result, the contact lens transfer device and method of the present invention can prevent the contact lens from collecting dirt, particles, germs and/or other unwanted particles that the contact lens otherwise might acquire from the fingers or hands of a user.

Other advantages of the present invention will become more readily apparent in view of the following detailed description of a currently preferred embodiment and accompanying drawings.

BRIEF DESCRIPTION OF THE DRAWINGS

FIGS. 1A through 1C are cross-sectional views of an embodiment of a contact lens transfer device of the present invention showing progressively the removal of a contact lens from the lens storage container onto the contact lens transfer device.

FIGS. 2A through 2C are cross-sectional views of the contact lens transfer device of FIGS. 1A through 1C showing progressively the transfer of the lens from the contact lens transfer device onto a contact lens holder of a contact lens applicator.

FIGS. 3A through 3D are somewhat schematic, cross-sectional views of a contact lens holder of a contact lens applicator that is usable with the contact lens transfer device of the present invention and showing progressively the transfer of a contact lens from the contact lens holder onto a user's eye (or cornea of the eye).

DETAILED DESCRIPTION

In FIGS. 1A through 1C, a contact lens transfer device used for transferring contact lenses onto a contact lens applicator is indicated generally by the reference numeral 10. The contact lens applicators that are used with the contact lens transfer device of the present invention may be any of the different types of applicators disclosed in U.S. Pat. No. 6,739,636, dated May 25, 2004, entitled "Contact Lens Applicator and Cartridge Used in Connection Therewith", U.S. application Ser. No. 10/851,865, filed May 21, 2004, entitled, "Contact Lens Applicator and Cartridge Used in Connection Therewith", U.S. application Ser. No. 60/573,996, filed May 24, 2004, entitled, "Apparatus for Applying and Removing Contact Lens and Related Method", and which are all assigned to the Assignee of the present invention and are hereby expressly incorporated by reference as part of the present disclosure. However, as may be recognized by those of ordinary skill in the pertinent art based on the teachings herein, the contact lens transfer device of the present invention may be used with other types of applicators or contact lens handling devices that are currently, or later become known.

The contact lens transfer device 10 comprises a body 12 and a button actuator 14 movably mounted within the body. The body 12 defines a central aperture 16 extending therethrough, an annular support flange 18 extending laterally inwardly into the central aperture 16, a peripheral external gripping surface 20 for gripping by a user's fingers, an annular alignment protuberance 22 formed on the base surface 24 of the body 12 and extending outwardly therefrom, and an upper surface 25 located on an opposite end of the body relative to the base surface 24.

The button actuator 14 includes a button 26 defining a peripheral flange 28 extending downwardly therefrom, a central recess 29, and an aperture 30 extending through the central recess. A tubular support 32 defines on one end a first peripheral support flange 34 that extends laterally from the support and is slidably received within the flange 28 of the button 26, and defines on the other end a second peripheral support flange 36 slidably received within the aperture 16 of the body on the opposite side of the body flange 18 relative to the first support flange 34. The tubular support 32 further defines a first open end 40 adjacent to the first peripheral support flange 34, a second open end 42 on the opposite end of the tubular support, and a first annular inner support surface 44 spaced axially between the first and second ends 40 and 42, respectively, of the support.

A lens holder 46 is received within the tubular support 32 and defines a first flange 48 slidably received within the button flange 28, an axially-extending bellows portion 50, a second annular inner support surface 52 that is axially engageable with the first annular inner support surface 44 of the tubular support 32, a substantially convex lens support surface 54 located on the opposite end of the lens holder relative to the first flange 48, an internal chamber 55, and at least one fluid-flow aperture 56 extending through the lens support surface 54 and in fluid communication with the internal chamber 55.

A coil spring 58 is seated within the axially-extending space 60 formed within the tubular support 32 and body 12, and extends axially between the first annular inner support surface 44 of the tubular support and the annular support flange 18 of the body 12 to bias the button actuator 14 outwardly of the body 12 (i.e., in a direction from the body toward the button).

With reference to FIGS. 1A through 1C, a contact lens "CL" is removed from a contact lens storage container 62 by first gripping the surface 20 of the body 12 with, for example, the index and third fingers of a hand, and simultaneously depressing inwardly with, for example, the thumb of the same hand, the button 26 to, in turn, cause the lens support surface 54 of the lens holder to extend axially outwardly of the body 12, as shown typically in FIG. 1B. Then, the axially-extending lens support surface 54 is lowered into the interior chamber 64 of the storage container until the lens support surface contacts the opposing surface of the contact lens CL. As indicated above, the lens storage container 62 may be the container in which the lens is stored and shipped by the manufacturer (such as a conventional plastic or blister pack container with a removable foil cover), or a conventional lens storage container that a user employs to store and/or disinfect or sterilize lenses overnight, for example. The lens is typically immersed in a liquid within such containers, such as a saline solution, or a multipurpose lens cleaning solution. Accordingly, when the lens supporting surface 54 is moved into the chamber 64 of the lens storage container 62, some of the liquid will flow onto the lens support surface and likely through the aperture 56 and into the interior of the lens holder. Then, once the lens support surface 54 contacts the opposing face of the contact lens "CL", the surface tension between the opposing surfaces will cause the lens to releasably secure itself to the lens support surface 54 with at least a film of liquid therebetween. As shown typically in FIG. 1C, the device 10 is then lifted away from the storage container 62 to remove the lens from the container. As also shown typically in FIG. 1C, the user may then release the button actuator 14, and the spring 58 will, in turn, drive the tubular support 32 outwardly of the body 12 until the second flange 36 of the body axially engages the body flange 18 (FIG. 1C).

A shown in FIGS. 2A through 2C, the contact lens applicator may include a housing 66 defining an open end 68 for receiving a contact lens holder 70 therethrough. As described in the above-mentioned co-pending patent application, the contact lens holder 70 is preferably connected to a drive mechanism (not shown) that moves the contact lens holder 70 axially through the opening 68 of the housing to, in turn, place a contact lens CL seated on the holder onto a user's eye. The housing 66 of the contact lens applicator preferably defines a first annular recess 72 on the outer end thereof. As shown in FIG. 2A, the first annular recess 72 receives therein the annular protuberance 22 of the body 12 of the contact lens transfer device 10 in order to align a lens CL releasably secured to the lens support surface 54 thereof with the lens holder 70 of the housing. The housing 66 also defines a second annular recess 74 spaced radially inwardly relative to the first annular recess 72 for receiving therein the open end of the tubular support 32 and thereby preventing further axial movement of the support, as described further below.

In order to transfer the contact lens from the transfer device 10 to the contact lens applicator, and as shown typically in FIG. 2A, the user places the body 12 of the transfer device onto the housing 66 of the applicator such that the protuberance 22 is received within the corresponding recess 72 to thereby align the contact lens CL with the lens holder 70. Then, as shown typically in FIG. 2B, the user presses the button 26 toward the body 12 of the transfer device to, in turn, move the lens support surface 54 and contact lens CL thereon into the aperture 68 of the housing. As the button 26 is depressed inwardly, the second end 42 of the tubular support 32 is received within the second annular recess 74 of the housing 66 and prevented from further inward axial movement. At this point, and as shown typically in FIG. 2B, the lens support surface 54 and contact lens CL thereon are spaced by a substantially fixed, predetermined axial distance from the corresponding lens support surface 76 of the applicator's lens holder 70. The user then continues to axially depress the button 26 toward the body 12 which, in turn, causes the bellows 50 of the lens holder 46 to axially compress. Compression of the bellows 50 increases the fluid pressure within the internal chamber 55 of the lens holder 46 and, in turn, delivers fluid (typically both air and liquid) from within the chamber, through the fluid-flow aperture 56, and into the interface between the contact lens CL and the lens support surface 54. If desired, the user may place a finger over the aperture 30 of the button 26 to increase the pressure within the chamber upon further depressing the button. As shown typically in FIG. 2C, the fluid introduced from the internal chamber 55, through the aperture 56, and into the interface between the contact lens CL and lens support surface 54, is sufficient to release the contact lens CL from the lens support surface 54 and allow the contract lens CL to drop onto the corresponding lens support surface 76 of the lens holder 70 of the contact lens applicator. The user then lifts the transfer device 10 away from the applicator housing 66, the spring 58 drives the actuator 14 outwardly of the housing and into the position shown in FIG. 1A, and the transfer device is ready to transfer another lens from a storage container onto a contact lens applicator.

In FIGS. 3A through 3D, another contact lens holder that may be movably mounted within a contact lens applicator is indicated generally by the reference numeral 170. The contact lens holder 170 is similar in many respects to the contact lens holder 70 described above, and therefore like reference numerals preceded by the numeral "1" are used to indicate like elements. A primary difference of the contact lens holder 170 is that the lens support surface 176 forms an annular surface having a relatively slight surface area in comparison to the surface area of the contact lens CL seated thereon to facilitate release of the contact lens from the holder and onto the eye. The contact lens holder 170 includes a base portion 178 that is connectable to a pusher (not shown) or like drive mechanism of the contact lens applicator to axially move the lens holder and lens seated thereon relative to the housing and onto a user's eye. A flexible bellows 180 extends between the lens support surface 176 and the base portion 178 to allow lens holder to flex axially, particularly when transferring the lens onto a user's eye. A fluid-flow aperture 182 extends through an approximately central portion of the lens support surface 176. As shown in FIGS. 3A and 3B, the contact lens applicator axially moves the contact lens CL onto the eye. In one mode of operation, when the lens contacts the eye, and as shown typically in FIG. 3C, the soft bellows 180 axially compresses. Compression of the bellows can cause fluid (air and/or liquid) within the interior of the bellows to flow outwardly through the aperture 182 and against the contact lens to, in turn, facilitate release of the lens from the lens support surface 176 and onto the eye. One advantage of this embodiment of the contact lens holder is that the surface area of the annular lens support surface 176 is relatively small, and thereby facilitates the release of the lens from lens holder onto an eye. Support portion 184 that extends laterally adjacent to annular lens support surface 176 facilitates maintaining a lens on the lens holder in the event the lens is moved laterally.

As may be recognized by those of ordinary skill in the pertinent art based on the teachings herein, numerous changes and modifications may be made to the above-described embodiment of the present invention without departing from the scope of the invention. For example, the components of the contact lens transfer device and/or of the contact lens applicator may take any of numerous different shapes and/or configurations, and/or may be made of any of numerous different materials that are currently or later become known for such components. Similarly, the contact lens holder of the transfer device may define any desired number of fluid-flow apertures or may include other structures that are currently or later become known for releasing a contact lens from the lens holder's support surface and transferring the lens into a contact lens applicator. Accordingly, this detailed description of a currently preferred embodiment is to be taken in an illustrative as opposed to a limiting sense.

The invention claimed is:

1. A contact lens transfer device for transferring a contact lens from a storage container to a contact lens applicator, comprising:
   a body;
   a contact lens holder movably mounted on the body and defining a contact lens support surface, at least one fluid-flow aperture extending through the contact lens support surface, and a chamber coupled in fluid communication with the at least one fluid-flow aperture, wherein a contact lens is removably receivable on the lens support surface, and the at least one fluid-flow aperture is coupled in fluid communication with an interface between the contact lens and lens support surface for introducing fluid from the chamber, through the fluid-flow aperture and into the interface to release the lens from the lens support surface; and
   a manually engageable actuator movably mounted relative to the body and drivingly coupled to the lens support surface for manually engaging the actuator and moving the lens support surface.

2. A contact lens transfer device as defined in claim 1, wherein the lens support surface is substantially convex, and defines a fluid-flow aperture extending through an approximately central portion thereof.

3. A contact lens transfer device as defined in claim 1, wherein the lens holder includes at least one movable portion coupled in fluid communication with the chamber and movable for, in turn, moving fluid from the chamber, through the fluid flow aperture, and into the interface between the contact lens support surface and a contact lens thereon.

4. A contact lens transfer device for transferring a contact lens from a storage container to a contact lens applicator, comprising:
   a body;
   a contact lens holder movably mounted on the body and including a contact lens support surface, at least one fluid-flow aperture extending through the contact lens support surface, a chamber coupled in fluid communication with the at least one fluid-flow aperture, and a bellows coupled in fluid communication with the chamber, wherein a contact lens is removably receivable on the lens support surface, the at least one fluid-flow aperture is coupled in fluid communication with an interface between the contact lens and lens support surface, and the bellows is movable for introducing fluid from the chamber, through the fluid-flow aperture and into the interface to release the lens from the lens support surface.

5. A contact lens transfer device as defined in claim 1, further comprising an approximately tubular support mounted between the lens holder and body for supporting the lens holder within the body.

6. A contact lens transfer device as defined in claim 5, further comprising a spring coupled between the tubular support and body for biasing the tubular support in a direction outwardly of the body.

7. A contact lens transfer device as defined in claim 6, further comprising an actuator coupled to the lens holder for moving the lens holder between (i) a retracted position, and (ii) an extended position for at least one of removing a contact lens from a storage container onto the lens support surface of the lens holder, and releasing the lens from the lens support surface onto a surface of a contact lens applicator.

8. A contact lens transfer device for transferring a contact lens from a storage container to a contact lens applicator, comprising:
   a body;
   a contact lens holder movably mounted on the body and defining a contact lens support surface, at least one fluid-flow aperture extending through the contact lens support surface, and a chamber coupled in fluid communication with the at least one fluid-flow aperture, wherein a contact lens is removably receivable on the lens support surface, and the at least one fluid-flow aperture is coupled in fluid communication with an interface between the contact lens and lens support surface for introducing fluid from the chamber, through the fluid-flow aperture and into the interface to release the lens from the lens support surface;
   an approximately tubular support mounted between the lens holder and body for supporting the lens holder within the body;
   a spring coupled between the tubular support and body for biasing the tubular support in a direction outwardly of the body; and
   a actuator defining a peripheral flange that slidably receives therein at least a portion of each of the tubular support and lens holder, wherein the button is coupled to the lens holder for moving the lens holder between (i) a retracted position, and (ii) an extended position for at least one of removing a contact lens from a storage container onto the lens support surface of the lens holder, and releasing the lens from the lens support surface onto a surface of a contact lens applicator.

9. A contact lens transfer device as defined in claim 1, in combination with a contact lens applicator including a housing, and a contact lens holder movably mounted on the housing, wherein one of the body of the contact lens transfer device and housing of the contact lens applicator defines a recess, and the other defines a raised portion receivable within the recess for aligning the lens support surface of the transfer device with the lens holder of the applicator.

10. A contact lens transfer device as defined in claim 9, further comprising an approximately tubular support mounted between the lens holder and body for supporting the lens holder within the body, and wherein the housing defines a stop surface that is engageable with a surface of the tubular support for preventing further movement of the support.

11. A contact lens transfer device for transferring a contact lens from a storage container to a contact lens applicator, comprising:
   first means for holding the device;
   second means movably mounted on the first means for supporting a contact lens thereon and defining an interface between the second means and a contact lens supported thereon;
   third means coupled in fluid communication with the second means for releasing a contact lens therefrom; and
   fourth means movably mounted relative to the first means and drivingly coupled to the second means for manually engaging the fourth means and moving the second means.

12. A contact lens transfer device as defined in claim 11, wherein the first means is a body defining an exterior surface that is manually engageable by a user, and an aperture for receiving therein the second means.

13. A contact lens transfer device as defined in claim 11, wherein the second means is a contact lens holder defining a lens support surface.

14. A contact lens transfer device for transferring a contact lens from a storage container to a contact lens applicator, comprising:
   first means for holding the device;
   second means movably mounted on the first means for supporting a contact lens thereon and defining an interface between the second means and a contact lens supported thereon and at least one fluid-flow aperture extending therethrough; and
   a chamber coupled in fluid communication with the at least one fluid-flow aperture of the second means, wherein a contact lens is removably receivable on the second means, and the at least one fluid-flow aperture is coupled in fluid communication with an interface between the contact lens and second means for introducing fluid from the chamber, through the fluid-flow aperture and into the interface to release the lens from the second means.

15. A method for transferring a contact lens from a storage container to a contact lens applicator, comprising:
   providing a contact lens transfer device including a body, a contact lens holder defining a contact lens support surface and at least one fluid-flow aperture extending through the contact lens support surface, and a manually engageable actuator movably mounted relative to the body and coupled to the lens support surface;
   manually engaging the manually engageable actuator of the contact lens transfer device;
   manually moving the actuator to place the lens support surface of the contact lens transfer device into contact with a contact lens received within a storage container;
   removing the lens support surface with the contact lens seated thereon from the storage container;
   positioning the lens support surface with the contact lens seated thereon adjacent to a lens holder of a contact lens applicator; and
   introducing a fluid into an interface between the lens support surface and contact lens seated thereon and, in turn, releasing the contact lens from the lens support surface and transferring the contact lens from the lens support surface onto the lens holder of the contact lens applicator.

16. A method as defined in claim 15, wherein the step of introducing fluid includes introducing liquid and air into the interface between the lens support surface and contact lens seated thereon.

17. A method as defined in claim 15, further comprising the step of manually engaging the manually engageable actuator to introduce the fluid.

* * * * *